United States Patent [19]
Hendrix

[11] Patent Number: 6,068,999
[45] Date of Patent: May 30, 2000

[54] DIETARY SUPPLEMENT FOR SUPPORTING CEREBROVASCULAR TONE AND TREATING MIGRAINE HEADACHES

[76] Inventor: Curt Hendrix, 17401 Ventura Blvd., Encino, Calif. 91316

[21] Appl. No.: 09/104,862

[22] Filed: Jun. 25, 1998

[51] Int. Cl.⁷ .................................................. A01N 65/00
[52] U.S. Cl. ........................................ 435/195.1; 514/468
[58] Field of Search ......................... 424/195.1; 514/468

[56] References Cited

U.S. PATENT DOCUMENTS

| | | | |
|---|---|---|---|
| 4,704,279 | 11/1987 | Hancock | 424/195.1 |
| 4,758,433 | 7/1988 | Johnson et al. | 424/195.1 |
| 5,273,759 | 12/1993 | Simmons | 424/465 |
| 5,384,121 | 1/1995 | Rhodes | 424/195.1 |
| 5,466,451 | 11/1995 | Beuscher et al. | 424/195.1 |
| 5,538,959 | 7/1996 | Mauskop | 514/165 |
| 5,905,089 | 1/1995 | Hwang et al. | 514/468 |

FOREIGN PATENT DOCUMENTS

96/22774   8/1996   WIPO .

OTHER PUBLICATIONS

Computer Abstract Caplus 1996:572066 Lazarowych et al WO9622774, Aug. 1, 1996.

*Primary Examiner*—Herbert J. Lilling
*Attorney, Agent, or Firm*—Michael J. Ram; Koppel & Jacobs

[57] ABSTRACT

The present invention relates to a dietary supplement for the support of normal cerebrovascular tone. Extracts of the feverfew plant in combination with magnesium and riboflavin, either singly or in combination provide the major therapeutic enhancement in the reduction of migraine headaches and the associated symptoms.

14 Claims, 1 Drawing Sheet

DIETARY SUPPLEMENT FOR SUPPORTING CEREBROVASCULAR TONE AND TREATING MIGRAINE HEADACHES

1. Field of the Invention

The present invention provides a dietary supplement which supplies a combination of prophylactic and restorative components which assist the body in maintaining normal cerebrovascular tone and reduces the symptoms of migraine headaches.

2. Background of the Invention

Migraine has been a well known medical problem for over 5,000 years and represents one of the most investigated types of head pain. Epidemiological research has shown that in the United States, 18% of women and 6% of men suffer from migraine headaches. This extrapolates to approximately 18 million females and 5.6 million males over the age of 12 with this disorder. The prevalence of migraine, according to the Center for Disease Control, has increased 60% from 1981 to 1989. While migraine can occur at any age, 30% of migraine sufferers report their first attack before the age of ten, and the condition is most common in adolescents and young adults. The economic impact of migraine is staggering, with annual cost of the disease estimated at 18 billion dollars.

The basic cause of migraine is still unknown. Although genetics may play a role, with 50 to 70% of migraine sufferers reporting a familial occurrence, no consistent biochemical or physiological characteristic has yet to be identified in the relatives of those afflicted with the conditions There are several pathophysiological views on the origin of migraine. While not mutually exclusive, these views include the a.Êvascular theory, b. central theory, c. neurogenic Inflammation theory and d. platelet theory.

a. Vascular Theory

In 1938, Graham and Wolff, two of the period's most preeminent headache researchers, developed the vascular hypothesis of migraine. They suggested that contraction of the intracranial arteries caused a reduction in blood flow to the visual cortex in the occipital lobe, resulting in the focal neurological symptoms ("aura") that accompany a migraine episode. As a consequence, the head pain that followed was the result of extra-cranial vasodilatation of the external carotid system, along with nerve compression in the carotid artery wall. These conclusions were based on the observation that the vasoconstricting drug ergotamine tartrate dampened pulsation of the superficial temporal artery (an end branch of the external carotid artery), resulting in migraine pain relief.

Despite the fact that the vascular model has been a dominant concept in migraine pathophysiology, several difficulties arising from this theory have been noted. These include the fact that during a common migraine attack, only minor changes in cerebral blood flow have been noted. Furthermore, oligemia, a phase of reduced blood flow, lasts for several hours longer than the aura. Lastly, the reduced blood flow is not sufficient to induce ischemia, alter neuronal function, and produce the aura phase. As a consequence of these criticisms, the central theory of migraine has been proposed.

b. Central Theory

The central theory suggests that spreading oligemia is the consequence of spreading neuronal depression, which begins as a result of decreased neuronal function in the occipital poles of the brain and progresses forward at a rate of two to three millimeters per minute. The spreading depression involves the depolarization of neurons and has associated with it marked cellular ionic abnormalities. The resulting lowered levels of cellular magnesium increase the likelihood of this type of spreading neuronal depression occurring. This repression of neural function results in a spreading oligemia that can last up to four to six hours. It progresses anteriorly, in a wave-like fashion, over the areas perfused by the middle and posterior cerebral arteries, temporarily impairing cortical vascular functioning. As a result, the aura of migraine may be the result of spreading depression, "a phenomenon originating within brain neurons and involving cerebral blood vessels only secondarily."

c. Neurogenic Inflammation Theory

While the concept of spreading neuronal depression and oligemia may explain the migraine aura, it does not account for the ensuing headache. Migraine head pain may be the result of inflammation in the trigeminovascular system (TVS). This theory suggests that the trigeminal nerve fibers innervating cranial vessels are an important component of an elaborate defense network protecting the brain from an actual or perceived insult. Inflammatory neurotransmitters such as substance P, calcitonin gene-related peptide and neurokinin A are released by the fifth cranial nerve. This release signals adjacent meningeal blood vessels to dilate. The resulting neurogenic inflammation sensitizes the neurons and this induces head pain. It is interesting to note that stimulation of the presynaptic serotonin receptor (5HT-1), blocks the release of substance P, thus preventing inflammation and pain.

Many researchers have felt that serotonin (5HT) is the specific neurochemical fuel of migraine. Platelets contain all of the 5HT normally present in blood, and, after they aggregate, 5HT is released, resulting in a potent vasoconstricting effect. During a migraine attack, platelet 5HT increases in the aura phase and diminishes in the headache phase. Following a migraine attack, this leads to an increase in urinary 5-hydroxyindolacetic acid (5-HIAA), the main metabolite of serotonin.

d. Platelet Theory

Many researchers have felt that serotonin (5HT) is the specific neurochemical cause of migraine. Platelets contain all of the 5HT normally present in blood, and after they aggregate, 5HT is released, resulting in a potent vasoconstricting effect. During a migraine attack, platelet 5HT increases in the aura phase and diminishes in the headache phase. Following a migraine attack, there is an increase in urinary 5-hydroxyindolacetic acid (5-HIAA), the main metabolite of serotonin. It is interesting to note that "serotonergic circuits are believed to be involved in modulation of sleep cycles, pain perception, and mood, all important factors in the pathogenesis of migraine." For example, "a decrease in the firing rate of serotonergic neurons of the midbrain dorsal raphe nucleus occurs with sleep, correlating with the observation that sleep often aborts a migraine attack."

However, serotonin may not be the only vasoactive chemical involved in the pathogenesis of migraine. Histamine, tyramine, catecholamines (norepinephrine and dopamine), prostaglandin E and free fatty acids may all have important roles to play in migraine pathogenesis.

EXISTING TREATMENTS—ABORTIVE THERAPY

For the migraine sufferer, there is a wide variety of therapeutic approaches both pharmacologic and non-pharmacologic. However, for practical reasons the management of migraine can be divided into a. abortive treatment and b. preventative treatment.

a. Abortive Treatment

An abortive treatment of migraine simply addresses the symptoms. only pharmacological interventions with analgesics and/or vasoconstrictors are effective for the acute attack. Initial therapy for mild migraine headache is usually aspirin or other nonsteroidal anti-inflammatory agents (e.g. ibuprofen and naproxen sodium). These analgesics, along with sleep in a quiet, ark room, an ice pack on the head and an antiemetic agent, are often sufficient to treat the mild migraine. The use of antiemetic drugs like metoclopramide (Reglan®), is an important variable in determining how effective analgesic action will be. Migraine attacks seem to cause atony and dilation of the stomach along with closure of the pyloric sphincter thereby impairing absorption of the analgesic medications. This decrease in absorption is probably why individuals with migraines generally complain about the lack of effectiveness of this class of drug. Metoclopramide not only helps with the nausea and the headache, but also improves gastrokinetics, correcting the delayed absorption. More potent vasoconstrictors, like ergotamine tartrate, are often combined with nonsteroidal, anti-inflammatory drugs and anti-emetic therapies for moderate to severe migraine attacks. Ergotamine is a potent vasoconstrictor that has been used since the 1920's as an abortive therapy for migraine episodes. While oral therapy can be employed, rectal suppositories of ergotamine are far more effective because it does not interfere with gastrointestinal function. A 1 mg rectal suppository has been shown to provide complete headache relief within three hours of taking the drug in 73% of patients with migraine.

However, despite ergotamine's effectiveness, it must be used intelligently, as frequent use of the drug results in rebound headache. Abstinence from the vasoconstricting medication for a few hours leads to vasodilation and headache pain. This then perpetuates a vicious cycle in which the patient gets daily headaches, and takes ergotamine on a daily basis. Other ergotamine side effects include nausea, vomiting, abdominal pain, muscle cramps, and occasionally, distal paresthesias. Individuals who take ergotamine on a daily basis may suffer from a condition called ergotism, whose symptoms includes nausea and weakness as well as cold, bluish and tingling extremities.

An intravenous derivative of ergotamine, dihydroergotamine (DHE), is an even more potent vasoconstrictor and is typically employed for headaches that persist or are severe in nature, despite initial oral abortive therapy. Both DHE and a new injectable drug called sumatriptan (Imitrex®), work by stimulating the inhibitory presynaptic 5HT receptor at the trigeminovascular junction. A dose of six milligrams of sumatriptan has been shown to reduce the intensity of moderate to severe migraine headaches by 70%. Side effects from this type of drug include distal paresthesias, tingling, heaviness, and a sensation of pressure.

b. Preventive Therapy

In contrast to abortive therapy, preventative drug strategies an be employed if the frequency of migraine attacks is sufficiently high. There are an extremely large number of medications available for migraine prophylaxis. Propanolol, verapamil and methysergide maleate are some of the more commonly employed drugs.

Propranolol is widely prescribed in the United States as a treatment for migraine prevention. Although it has proven to be effective in migraine prophylaxis, its side effects include fatigue, depression, impotence, insomnia, dizziness, and cold extremities.

Another class of antihypertensive medications like propranolol are the calcium channel blockers. Calcium channel blockers were introduced as a class of preventative migraine medications to help antagonize vasoconstriction and prevent cerebral hypoxia. However, research has suggested that they may not be as effective as beta-blockers and, furthermore, that they are associated with numerous adverse events including constipation, fluid retention, drowsiness and hypotension.

Unlike calcium channel blockers or beta-blockers, methysergide is a potent, type 2 serotonin antagonist. For migraine prophylaxis, studies have shown that a 6 mg dose reduces migraine occurrence by more than half in 60% of the patients. However, long-term use of this drug may not be warranted as it is associated with retroperitoneal fibrosis. As such, a drug hiatus for two to four weeks following six months of continuous use is recommended.

Like pharmacological intervention, non-pharmacological prophylactic therapies may also be highly effective. These include behavioral modification techniques such as stress management, biofeedback, exercise, acupuncture, trigger point injections and numerous physical therapy techniques There is currently no formulation which addresses satisfactorily the needs of a those who suffer from migraine headaches. Many of the existing formulations can cause significant side effects. Because of the apparent multi-faceted etiology, some formulations work well for some people but not others.

SUMMARY OF THE INVENTION

The present invention comprises several unique and novel combinations of the following components in a single formulation: an extract of the Feverfew plant, a magnesium salt and riboflavin or as an alternative embodiment, an extract of the Feverfew plant in combination with a magnesium salt or riboflavin.

DESCRIPTION OF THE DRAWINGS

The invention will be further described with reference to the accompanying drawing in which.

DETAILED DESCRIPTION OF THE INVENTION

Figure 1:
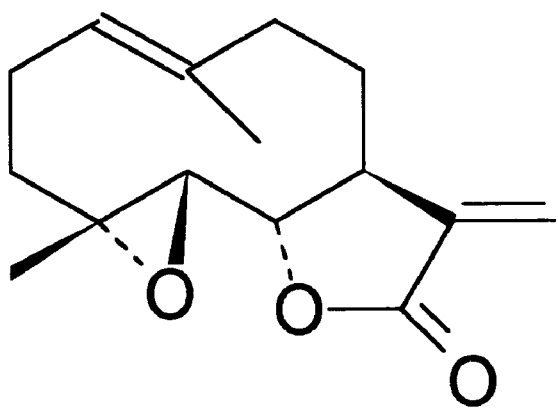
FIG. 1 is a representation of the chemical structure of arthenolide, a major component of the feverfew extracts.

Formulating an effective treatment for any disease, especially one as challenging as migraine headaches, always is difficult. What cause or causes should be addressed and how to best address them, are just some of these difficulties. Many compounds have been tested against migraine headaches, some with encouraging results. But which to use, especially in combination with which others, is a most challenging question.

The present invention is based on a particular combination of compounds, each in a particular dosage range. Tests have shown that this combination to be uniquely effective as a dietary supplement in treating migraine headaches.

It should be noted that all of the components of this invention are available commercially from various vendors and that the extracts are standardized to various components normally found within the extract. The Feverfew extract is preferably obtained from Indena, U.S.A, Inc., of Seattle, Wash.

The invention is usually provided in a tablet, but can also be provided in other forms including soft-get capsule, powder or other methods of packaging. Actual formulation into capsules is handled using industry standard methods of production.

The details of the individual components of the present invention are described below.

Feverfew

Feverfew (*Tanacetum parthenium*) is a member of the daisy family (Asteraceae) and is a short, bushy perennial that grows along fields and roadsides. Its yellow-green leaves and yellow flowers resemble those of chamomile, for which it is sometimes confused. The flowers bloom from July to October. The leaves are used in medicinal preparations. Feverfew enjoyed wide use by British herbalists as an analgesic in the treatment of fevers and arthritis, but faded into obscurity. Feverfew has enjoyed a revival over the past two decades due to approval of its use for treatment of migraine by both the Canadian and British governments. Active Constituents Feverfew is rich in compounds known as sesquiterpene lactones (STL). The most important of these compounds is parthenolide (see FIG. 1). First identified in 1960, parthenolide represents about 85% of the STL content in feverfew and is the portion of the leaf believed to be responsible for feverfew's anti-migraine activity.

A critical consideration in commercial feverfew products has been the highly variable content of parthenolide. An analysis of commercial feverfew products in Canada found about half are virtually devoid of this compound. As a minimal standard, the Health Protection Branch of the Health and Welfare Department of the Canadian Government has proposed that feverfew preparations should contain at least 0.2% parthenolide content.

Mechanism of Action

Feverfew, and specifically parthenolide, inhibits platelet aggregation and histamine release. It has also been shown to inhibit release of serotonin from platelets and polymorphonuclear leukocyte granules. This is believed to reduce the severity, duration and frequency of migraine headaches and lead to an improvement in blood vessel tone.

Feverfew also inhibits prostaglandin synthesis and the release of arachidonic acid. This action may explain its historical use for inflammatory conditions such as arthritis.

Clinical Applications

Clinical studies with feverfew have focused on the treatment and prevention of migraine and have primarily taken place in Great Britain. These studies indicate the efficacy of feverfew as a useful tool in the long-term management of migraines.

The initial clinical study enrolled migraine patients who had been using feverfew for several years. Seventeen patients were enrolled and given either feverfew (50 mg daily) or placebo. Eight patients, who remained on feverfew, experienced continued relief of migraines over a six month period. The nine receiving placebo had an almost three-fold increase in migraines. Many of these headaches were incapacitating, and anxiety, insomnia and muscle and joint soreness were also reported. This has prompted some concern at the abrupt cessation of feverfew therapy.

A second study enrolled 72 migraine sufferers. They received either 82 mg of feverfew (containing approximately 500 mcg of parthenolide) daily or placebo. Treatment with feverfew for four months led to a decreased incidence and severity of migraines. Feverfew also led to less vomiting attacks and fewer visual disturbances during migraine attacks. Adverse events were mild (primarily mild gastrointestinal nervousness) and did not result in discontinuation of treatment.

Previously Recommended Dosages Appropriate dosing of feverfew leaf for migraine prophylaxis is based on parthenolide content. The Canadian Health Protection Branch has granted a Drug Identification Number (DIN) for feverfew. They recommend a daily dosage of 125 mg of a dried feverfew leaf preparation from authentic Tanacetum parthenium containing a minimum of 0.2% parthenolide for migraine prevention. This translates to a daily parthenolide dosage of at least 250 mcg. This should be considered a minimum amount for efficacy. Whether considerably higher doses of parthenolide might offer greater results has yet to be proven. Continuous use for at least four to six weeks is recommended.

Side Effects/Contraindications

In addition to the adverse events listed in the clinical studies above, the most common side effect reported with feverfew has been mouth ulceration. This has predominantly been found in individuals chewing the leaves. Scattered reports of dermatitis have been reported with use of feverfew. To date, no long-term toxicity studies have been performed.

Magnesium

Research had indicated that various factors which are known to trigger migraines (namely stress, pregnancy, menstruation, alcohol ingestion, and some diuretics) also promote magnesium wasting. In addition, magnesium exerts many of the same effects as drugs that are helpful in the prevention or treatment of migraines. These effects include: (1) inhibition of vasospasm; (2) inhibition of platelet aggregation; (3) stabilization of cell membranes; (4) interference with the synthesis, release or action of inflammatory mediators; and (5) alterations in cerebral vascular tone. In addition, brain magnesium concentrations (as measured by NMR spectroscopy) were significantly lower by 19% in patients during a migraine attack than in healthy controls. These observations suggest that magnesium may play a role in the prevention and/or treatment of migraine.

Magnesium has also been given intravenously to treat acute episodes of migraine. Forty patients with an acute migraine attack were given 1.0 g of magnesium sulfate (in a 1.0% solution) over five minutes. Fifteen minutes after the infusion, 35 patients (87.5%) experienced at least a 50% reduction in pain. Nine patients (22.5%) had complete relief of pain. In 21 of the 35 patients who improved, relief persisted for 24 hours or more. The effectiveness of magnesium was related to the pretreatment serum concentration of ionized magnesium. Of the 21 patients whose serum ionized magnesium level was below 0.54 mmol/l, pain relief lasted at least 24 hours in 18 cases (86%). In contrast, lasting relief occurred in only 3 (16%) of 19 patients whose serum ionized magnesium concentration was at or above 0.54 mmol/l ($p<0.001$). This study suggests that intravenous administration of magnesium is an effective treatment for acute migraine attacks, particularly in patients whose serum ionized magnesium concentrations are low.

These studies provide a rationale for oral magnesium supplementation for migraine prophylaxis. A reasonable dosage is 200 to 600 mg/day. Intravenous administration of magnesium may also be considered as a method of aborting acute migraine attacks. While measurement of serum ionized magnesium might be useful to predict which patients are most likely to respond to intravenous magnesium, this test is not yet commercially available.

Riboflavin

Riboflavin is the precursor of flavin adenine dinucleotide (FAD), a coenzyme involved in the electron-transport chain. A deficiency of mitochondrial energy reserve has been observed between attacks in patients with migraines. Theoretically, this defect might be ameliorated by compounds such as riboflavin which enhance the activity of the electron-transport chain.

To test that theory, 49 patients with recurrent migraines were given riboflavin, 400 mg/day with breakfast, for at least three months. The mean number of migraine attacks fell by 67% and mean migraine severity improved by 68%. One patient stopped treatment because of gastric intolerance, but no other side effects were reported. This study suggests that riboflavin supplementation may reduce the recurrence rate of migraines.

Although data on the effect of riboflavin remain preliminary, this vitamin is inexpensive and safe.

Preferred Embodiment

From these and other studies, it appears that a combination of feverfew extract with a therapeutically effective amount of STL, particularly parthenolide, combined with either or both, therapeutically effective amounts of magnesium and riboflavin, is especially effective in treating migraine headache.

The preferred embodiment is a unit dosage form, which could be a tablet, a measured amount of powder, a capsule or other like form, containing a composition comprised of the following components:

1. 50 milligrams of feverfew extract standardized to 0.7% parthenolide, and
2. 150 milligrams of Magnesium preferably as a 1:1 ratio of magnesium citrate and magnesium oxide, and
3. 200 milligrams of riboflavin.

With this embodiment, the unit dose should be taken as a dietary supplement, two times each day to provide the desired level of treatment of a daily dosage of 100 mg of a feverfew extract, 300 mg of magnesium and 400 mg of riboflavin.

It is clear from studies, that the amount of each of the components administered on a per unit time basis is the important factor. How the components are distributed between dosage form and the actual number is not important.

Likewise, the actual percentage of STL, as measured by parthenolide, within the Feverfew extract could vary over a reasonable range as long as the actual amount of the Feverfew extract is adjusted in order to provide the same therapeutically effective dose.

Studies with the preferred embodiment has shown a significantly greater percentage of symptomatic relief that would be expected from the individual components alone. In addition to the improved cerebrovascular tone, patients receiving the preferred embodiment have significantly reduced occurrence of migraine headaches, decreased sensitivity to light and sound, reduced nausea and increased mobility.

As an alternative to the preferred embodiment, combinations of Feverfew extract and either riboflavin or magnesium are also believe to be effective in reducing the symptoms of migraine headaches.

No previously known dietary supplement has provided in a single treatment the wide range of therapeutic benefits that are provided by the instant invention. All components have been included in the present invention at known therapeutically effective amounts in order to provide broad spectrum therapeutic benefits with minimal side effects. Though the preferred embodiment includes feverfew extract, riboflavin and magnesium, combinations of feverfew extract plus riboflavin and feverfew extract plus magnesium, should also prove effective.

In addition, having all components available in a single formulation provides cost savings for the patient and more efficient treatment protocols for the physician.

Case History #1

This patient is a 30 year old woman who has had a seven year history of migraines. Typically she would wake in the morning with a migraine headache which would only get worse as the day wore one. The headaches in the morning would include sharp razor like pains in the right eye and intense throbbing headache on the right side of her head. Often a mild migraine would always progress into a full on migraine which included extreme sensitivity to light and sound and nausea which would result in vomiting 10–20 times a day.

After using the preferred embodiment as a dietary supplement, the occurrence rate was significantly reduced with mild occurrences often dissipating without escalating to a full migraine and often without the use of prescription medicines. In addition, the nausea was absent. The patient's mobility was enhanced significantly. While suffering a full migraine, the patient would be bed-ridden because of hypersensitivity to light, sound and movement. While under treatment with the preferred embodiment, the patient was no longer bed ridden by the migraine attacks and was able to sit, stand, work and walk slowly.

The reduction of the nausea has permitted the patient, when needed, to take Imitrex®, a prescription medicine. Previously, the nausea was so severe that the patient couldn't keep the medicine down long enough to provide any therapeutic effect.

Case History #2

A 40 year old female patient has suffered migraine headaches since puberty. The frequency has ranged from 2 to 10 a month and lasting from a few hours to as long as 40 days.

Patient has sought medical advice from various doctors, therapists and even a neurologist who specialized in headaches. Patient has tried a wide range of therapeutic techniques and devices including biofeedback, meditation and relaxation techniques, physical therapy, chiropractic treatments, acupuncture, acupressure, exercise, and dietary modifications.

The patient has taken beta blockers, inhalers, Midrin, Imitrex® injections, Fiorinal and Demerol injections. All of which had varying success with varying side effects.

After using the preferred daily dosage, the patient was migraine free for the first two months. On longer use, the patient rarely had migraine headaches, and when she does, the pain is much less severe and the duration is much less.

Although the invention has been described with reference to particular disclosures, it is to be understood that the invention is not limited to these particular disclosures and extends to all equivalents within the scope of the claims.

I claim:

1. A dietary supplement comprising
   an extract from the feverfew plant,
   magnesium, and
   riboflavin,
      wherein the feverfew extract contains about 0.7% parthenolide and the magnesium is provided as a combination of magnesium oxide and magnesium citrate.

2. A dietary supplement comprising
   an extract from the feverfew plant, and magnesium
      wherein the feverfew extract contains about 0.7% parthenolide and the magnesium is provided as a combination of magnesium oxide and magnesium citrate.

3. The dietary supplement as set forth in claim 1, wherein said feverfew extract is present in an amount of about 50 milligrams per unit dose, said magnesium is present in an amount of about 150 milligrams per unit dose, and said riboflavin is present in an amount of about 200 milligrams per unit dose.

4. The dietary supplement as set forth in claim 2, wherein said feverfew extract is present in an amount of about 50 milligrams per unit dose, and said magnesium is present in an amount of about 150 milligrams per unit dose.

5. The dietary supplement as set forth in claim 3, wherein said magnesium further comprises a one to one ratio of magnesium citrate and magnesium oxide.

6. A dietary supplement as set forth in claim 4, wherein said magnesium further comprises a one to one ratio of magnesium citrate and magnesium oxide.

7. The dietary supplement of claim 3, wherein a daily dosage is at least two unit doses.

8. The dietary supplement of claim 4, wherein a daily dosage is at least two unit doses.

9. A method for reducing the symptoms of migraine headaches comprising administering a therapeutically effective amount of a dietary supplement comprising:

an extract of the feverfew plant riboflavin and magnesium wherein the extract from the feverfew plant contains about 0.7% parthenolide and the magnesium is provided as a combination of magnesium oxide and magnesium citrate.

10. The method for reducing the symptoms of migraine headaches as set forth in claim 9, wherein said therapeutically effective dose is a daily dosage of feverfew extract of about 100 milligrams, of riboflavin of about 400 milligrams, and of magnesium of about 300 milligrams.

11. The method of claim 9, wherein the magnesium oxide and the magnesium citrate are present in a ratio of about one to one.

12. A method of reducing the symptoms of migraine headaches comprising administering a therapeutically effective amount of a dietary supplement comprising:

an extract of feverfew plant, and magnesium wherein the extract of feverfew plant contains about 0.7% parthenolide and the magnesium is provided as a combination magnesium oxide and magnesium citrate.

13. A method of reducing the symptoms of migraine headaches comprising the steps of administering a therapeutically effective amount of a dietary supplement comprising:

an extract of feverfew plant, and magnesium wherein the magnesium is provided as a combination magnesium oxide and a magnesium salt of an organic acid.

14. The method of claim 12 wherein the magnesium oxide and the magnesium citrate are present in a ratio of about one to one.

* * * * *